(12) United States Patent
Dolan et al.

(10) Patent No.: US 6,610,124 B1
(45) Date of Patent: Aug. 26, 2003

(54) HEAVY HYDROCARBON RECOVERY FROM PRESSURE SWING ADSORPTION UNIT TAIL GAS

(75) Inventors: William Bachop Dolan, Yardley, PA (US); Michael J. Mitariten, Pittstown, NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 10/094,716

(22) Filed: Mar. 12, 2002

(51) Int. Cl.$^7$ ............................................. B01D 53/047
(52) U.S. Cl. ................. 95/98; 95/105; 95/130; 95/139; 95/143
(58) Field of Search ............. 95/96–106, 130, 95/139, 900, 902, 141, 143

(56) References Cited

U.S. PATENT DOCUMENTS

| | | | |
|---|---|---|---|
| 2,843,219 A | 7/1958 | Habgood et al. | |
| 3,430,418 A | * 3/1969 | Fuderer | 95/100 |
| 3,738,087 A | * 6/1973 | McCombs | 95/98 |
| 3,751,878 A | 8/1973 | Collins | 55/58 |
| 4,077,779 A | 3/1978 | Sircar et al. | 55/25 |
| 4,475,929 A | * 10/1984 | Fuderer | 95/97 |
| 4,589,888 A | * 5/1986 | Hiscock et al. | 95/100 |
| 4,770,676 A | 9/1988 | Sircar et al. | 55/26 |
| 4,784,672 A | 11/1988 | Sircar | 55/26 |
| 4,857,083 A | 8/1989 | DiMartino | 55/26 |
| 4,915,711 A | 4/1990 | Kumar | 55/26 |
| 4,938,939 A | 7/1990 | Kuznicki | 423/326 |
| 4,964,888 A | 10/1990 | Miller | 55/58 |
| 4,964,889 A | 10/1990 | Chao | 55/58 |
| 5,026,406 A | 6/1991 | Kumar | 55/26 |
| 5,089,034 A | * 2/1992 | Markovs et al. | 95/99 |
| 5,133,785 A | * 7/1992 | Kumar et al. | 95/101 |
| 5,234,472 A | 8/1993 | Krishnamurthy et al. | 95/98 |
| 5,354,346 A | 10/1994 | Kumar | 95/101 |
| 5,382,280 A | 1/1995 | Choe et al. | 95/98 |
| 5,453,263 A | * 9/1995 | Blosser et al. | 423/713 |
| 5,547,492 A | * 8/1996 | Cho et al. | 95/100 |
| 5,560,763 A | * 10/1996 | Kumar | 95/98 |
| 5,669,960 A | * 9/1997 | Couche | 95/96 |
| 5,840,099 A | * 11/1998 | Kratz et al. | 95/101 |
| 5,912,422 A | * 6/1999 | Bomard et al. | 95/96 |
| 5,938,819 A | 8/1999 | Seery | 95/104 |
| 5,989,316 A | 11/1999 | Kuznicki et al. | 95/103 |
| 5,993,517 A | 11/1999 | Chen et al. | 95/98 |
| 6,068,682 A | 5/2000 | Kuznicki et al. | 95/130 |
| 6,090,738 A | * 7/2000 | Choudary et al. | 502/62 |
| 6,197,092 B1 | 3/2001 | Butwell et al. | 95/96 |
| 6,290,751 B1 | 9/2001 | Ragil et al. | 95/101 |
| 6,315,817 B1 | 11/2001 | Butwell et al. | 95/96 |
| 6,319,303 B1 | * 11/2001 | Guillard et al. | 95/97 |
| 6,387,159 B1 | * 5/2002 | Butwell et al. | 95/99 |
| 6,497,750 B2 | * 12/2002 | Butwell et al. | 95/96 |

* cited by examiner

Primary Examiner—Robert H. Spitzer
(74) Attorney, Agent, or Firm—Russell G. Lindenfeldar

(57) ABSTRACT

A pressure swing adsorption process for the separation of impurities such as nitrogen and carbon dioxide and recovery of hydrocarbons from a natural gas stream utilizes two separate adsorption systems, the first containing an adsorbent selective for nitrogen, carbon dioxide or both and the second containing a hydrocarbon-selective adsorbent. In the process, the natural gas stream is passed through a first adsorbent to form a product stream enriched with methane and to adsorb nitrogen and/or carbon dioxide and which further co-adsorbs at least a portion of the hydrocarbons contained in the feed stream. The hydrocarbons are recovered by passing a low pressure waste stream from the first pressure swing adsorption stage which contains co-adsorbed nitrogen and/or carbon dioxide and hydrocarbons and directing the waste stream to the second pressure swing adsorption stage to adsorb the hydrocarbons and produce a product stream enriched in nitrogen and/or carbon dioxide. The hydrocarbons are recovered from the hydrocarbon-selective adsorbent by an intermediate pressure methane-containing stream from the first pressure swing adsorption stage which purges the adsorbent in the second stage and forms a combined stream comprising methane and $C_{3+}$ hydrocarbons. The $C_{3+}$ hydrocarbons can be separated from the methane such as by compression with flash separation or refrigeration.

42 Claims, 3 Drawing Sheets

HEAVY HYDROCARBON RECOVERY FROM PRESSURE SWING ADSORPTION UNIT TAIL GAS

FIELD OF THE INVENTION

This invention relates to the purification of natural gas, and, more particularly, to the removal of nitrogen and/or carbon dioxide and recovery of $C_{3+}$ hydrocarbon from natural gas by use of a novel pressure swing adsorption (PSA) process.

BACKGROUND OF THE INVENTION

The removal of nitrogen and acid gases such as carbon dioxide from natural gas is of considerable importance inasmuch as nitrogen and carbon dioxide can be present to a significant extent. Nitrogen and carbon dioxide contamination lower the heating value of the natural gas and increase the transportation cost based on unit heating value.

Applications aimed at removing nitrogen, carbon dioxide, and other impurities from natural gas steams streams provide significant benefits to the U.S. economy. In 1993, the Gas Research Institute (GRI) estimated that about one third of the natural gas reserves in the U.S. are defined as sub-quality due to contamination with nitrogen, carbon dioxide, and sulfur. Many of these reserves, however, have discounted market potential, if they are marketable at all, due to the inability to cost effectively remove the nitrogen and carbon dioxide. Nitrogen and carbon dioxide are inert gases with no BTU value and must be removed to low levels (4% total inerts typically and 2% carbon dioxide) before the gas can be sold.

Concurrently, the U.S. has proven reserves of natural gas totaling 167 trillion cubic feet. Over the past five years, annual consumption has exceeded the amount of new reserves that were found. This trend could result in higher cost natural gas and possible supply shortages in the future. As the U.S. reserves are produced and depleted, finding new, clean gas reserves involves more costly exploration efforts. This usually involves off shore exploration and/or deeper drilling onshore, both of which are expensive. Moreover, unlike crude oil, it is expensive to bring imports of natural gas into North America, therefore pricing of natural gas could be expected to rise forcing end users to seek alternative fuels, such as oil and coal, that are not as clean burning as gas. While base consumption for natural gas in the U.S. is projected to grow at 2–3% annually for the next ten years, one segment may grow much more rapidly. Natural gas usage in electric power generation is expected to grow rapidly because natural gas is efficient and cleaner burning allowing utilities to reduce emissions. Accordingly, there is a need to develop a cost-effective method of upgrading currently unmarketable sub-quality reserves in the U.S. thereby increasing the proven reserve inventory.

Methods heretofore known for purification of natural gas, in particular, nitrogen removal, may be divided roughly into three classifications:

(a) Methods involving fractional distillation at low temperature and (usually) high pressure, i.e. cryogenics. Since nitrogen has a lower boiling point than methane and the other hydrocarbons present in natural gas, it may be removed as a gas on liquefying the remaining constituents which are then revaporized.

(b) By selective adsorption of the methane and higher hydrocarbons on an adsorbent such as activated carbon. The adsorbed gases are then desorbed to give a gas free of nitrogen.

(c) Miscellaneous processes involving selective diffusion through a series of organic membranes, formation of lithium nitride by treatment with lithium amalgam, absorption of the nitrogen in liquid ammonia or in liquid sulfur dioxide.

The principal disadvantage of the fractional distillation and adsorption processes is that they remove the major component, methane, from the minor component, nitrogen, instead of the reverse. In cryogenic processing, almost the entire volume of natural gas must be refrigerated, usually compressed, and then heated again. Accordingly, cryogenic processing is expensive to install and operate, limiting its application to a small segment of reserves. Cryogenic technology is believed only capable of cost effectively purifying reserves, which exceed 50,000,000 standard cubic feet of gas per day. Gas reserves that do not fit these criteria are not currently being purified. The potential value of this gas.is totally lost as the wells are usually capped. The processes suggested under paragraph (c) above are handicapped by an unsatisfactory degree of separation or by the use of very expensive materials.

In smaller-scale natural gas operations as well as in other areas such as synthesis gas and coke oven gas processing, adsorption processes can be especially well suited. The adsorption capacities of adsorption units can, in many cases, be readily adapted to process gas mixtures of varying nitrogen content without equipment modifications, i.e. by adjusting adsorption cycle times. Moreover, adsorption units can be conveniently skid-mounted, thus providing easy mobility between gas processing locations. Further, adsorption processes are often desirable because more than one component can be removed from the gas. As noted above, nitrogen-containing gases often contain other gases that contain molecules having smaller molecular dimensions than nitrogen, e.g., for natural gas, carbon dioxide, oxygen and water.

U.S. Pat. No. 2,843,219 discloses a process for removing nitrogen from natural gas utilizing zeolites broadly and contains specific examples for the use of zeolite 4A. The process disclosed in the patent suggests use of a first nitrogen selective adsorbent zeolite in combination with a second methane selective adsorbent. The molecular sieve adsorbent for removing nitrogen is primarily regenerated during desorption by thermal swing. A moving bed adsorption/desorption process is necessary for providing sufficient heat for the thermal swing desorption. The moving bed process specifically disclosed in this patent is not practical and it does not provide a cost efficient method for the separation of nitrogen from natural gas in view of high equipment and maintenance costs and degradation of the adsorbent by attrition due to contact with the moving adsorbent particles.

Despite the advantageous aspects of adsorption processes, the adsorptive separation of nitrogen from methane has been found to be particularly difficult. The primary problem is in finding an adsorbent that has sufficient selectivity for nitrogen over methane in order to provide a commercially viable process. In general, selectivity is related to polarizability, and methane is more polarizable than nitrogen. Therefore, the equilibrium adsorption selectivity of essentially all known adsorbents such as large pore zeolites, carbon, silica gel, alumina, etc. all favor methane over nitrogen. However, since nitrogen is a smaller molecule than methane, it is possible to have a small pore zeolite which adsorbs nitrogen faster than methane. Clinoptilolite is one of the zeolites which has been disclosed in literature as a rate selective adsorbent for the separation of nitrogen and methane.

U.S. Pat. No. 4,964,889 discloses the use of natural zeolites such as clinoptilolites having a magnesium cation content of at least 5 equivalent percent of the ion-exchangeable cations in the clinoptilolite molecular sieve for the removal of nitrogen from natural gas. The patent discloses that the separation can be performed by any known adsorption cycle such as pressure swing, thermal swing, displacement purge or nonadsorbable purge, although pressure swing adsorption is preferred. However, this patent is silent as to specifics of the process, such as steps for treating the waste gas, nor is there disclosure of a high overall system recovery.

It is well-known to remove acid gases such as hydrogen sulfide and carbon dioxide from natural gas streams using an amine system wherein the acid gases are scrubbed from the feed with an aqueous amine solvent with the solvent subsequently stripped of the carbon dioxide or other acid gases with steam. These systems are widely used in industry with over 600 large units positioned in natural gas service in the U.S. The amine solvent suppliers compete vigorously and the amines used range from DEA to specialty formulations allowing smaller equipment and operating costs while incurring a higher solvent cost. These systems are well accepted although they are not very easy to operate. Keeping the amine solvents clean can be an issue.

Another disadvantage to using aqueous amines is that the natural gas product of an aqueous amine system is water saturated. Accordingly, dehydration typically using glycol absorption would be required on the product stream after the carbon dioxide has been removed adding operational and capital costs to the purification process.

For smaller volume applications where gas flows are less than five to ten million cubic feet per day, considerable attention has been given to the development of pressure swing adsorption (PSA) processes for removal of gaseous impurities such as $CO_2$.

Numerous patents describe PSA processes for separating carbon dioxide from methane or other gases. One of the earlier patents in this area is U.S. Pat. No. 3,751,878, which describes a PSA system using a zeolite molecular sieve that selectively adsorbs $CO_2$ from a low quality natural gas stream operating at a pressure of 1000 psia, and a temperature of 300° F. The system uses carbon dioxide as a purge to remove some adsorbed methane from the zeolite and to purge methane from the void space in the column. U.S. Pat. No. 4,077,779, describes the use of a carbon molecular sieve that adsorbs $CO_2$ selectively over hydrogen or methane. After the adsorption step, a high pressure purge with $CO_2$ is followed by pressure reduction and desorption of $CO_2$ followed by a rinse at an intermediate pressure with an extraneous gas such as air. The column is then subjected to vacuum to remove the extraneous gas and any remaining $CO_2$.

U.S. Pat. No. 4,770,676, describes a process combining a temperature swing adsorption (TSA) process with a PSA process for the recovery of methane from landfill gas. The TSA process removes water and minor impurities from the gas, which then goes to the PSA system, which is similar to that described in U.S. Pat. No. 4,077,779 above, except the external rinse step has been eliminated. $CO_2$ from the PSA section is heated and used to regenerate the TSA section. U.S. Pat. No. 4,857,083, claims an improvement over U.S. Pat. No. 4,077,779 by eliminating the external rinse step and using an internal rinse of secondary product gas ($CO_2$) during blowdown, and adding a vacuum for regeneration. The preferred type of adsorbent is activated carbon, but can be a zeolite such as 5A, molecular sieve carbons, silica gel, activated alumina or other adsorbents selective of carbon dioxide and gaseous hydrocarbons other than methane.

U.S. Pat. No. 4,915,711, describes a PSA process that uses adsorbents from essentially the same list as above, and produces two high purity products by flushing the product (methane) from the column with the secondary product (carbon dioxide) at low pressure, and regenerating the adsorbent using a vacuum of approximately 1 to 4 psia. The process includes an optional step of pressure equalization between columns during blowdown. U.S. Pat. No. 5,026,406 is a continuation-in-part of U.S. Pat. No. 4,915,711 with minor modifications of the process.

U.S. Pat. No. 5,938,819 discloses removing $CO_2$ from landfill gas, coal bed methane and coal mine gob gas, sewage gas or low quality natural gas in a modified PSA process using a clinoptilolite adsorbent. The adsorbent has such a strong attraction to $CO_2$ that little desorption occurs even at very low pressure. There is such an extreme hysteresis between the adsorption of the adsorbent and desorption isotherms, regeneration of the adsorbent is achieved by exposure to a stream of dry air.

In general, first applications of PSA processes were performed to achieve the objective of removing smaller quantities of adsorbable components from essentially non-adsorbable gases. Examples of such processes are the removal of water from air, also called heatless drying, or the removal of smaller quantities of impurities from hydrogen. Later this technology was extended to bulk separations such as the recovery of pure hydrogen from a stream containing 30 to 90 mole percent of hydrogen and other readily adsorbable components like carbon monoxide or dioxide, or, for example, the recovery of oxygen from air by selectively adsorbing nitrogen onto molecular sieves.

PSA processes are typically carried out in multi-bed systems as illustrated in U.S. Pat. No. 3,430,418 to Wagner, which describes a system having at least four beds. As is generally known and described in this patent, the PSA process is commonly performed in a cycle of a processing sequence that includes in each bed: (1) higher pressure adsorption with release of product effluent from the product end of the bed; (2) co-current depressurization to intermediate pressure with release of void space gas from the product end thereof; (3) countercurrent depressurization to a lower pressure; (4) purge; and (5) pressurization. The void space gas released during the co-current depressurization step is commonly employed for pressure equilization purposes and to provide purge gas to a bed at its lower desorption pressure.

Similar systems are known which utilize three beds for separations. See, for example, U.S. Pat. No. 3,738,087 to McCombs. The faster the beds perform steps 1 to 5 to complete a cycle, the smaller the beds can be when used to handle a given hourly feed gas flow. If two steps are performed simultaneously, the number of beds can be reduced or the speed of cycling increased; thus, reduced costs are obtainable.

U.S. Pat. No. 4,589,888 to Hiscock, et. al. discloses that reduced cycle times are achieved by an advantageous combination of specific simultaneous processing steps. The gas released upon co-current depressurization from higher adsorption pressure is employed simultaneously for pressure equalization and purge purposes. Co-current depressurization is also performed at an intermediate pressure level, while countercurrent depressurization is simultaneously performed at the opposite end of the bed being depressurized.

The present assignee has developed an effective PSA process for the removal of nitrogen from natural gas streams.

The process is described in U.S. Pat. No. 6,197,092, issued Mar. 6, 2001. In general, the process involves a first pressure swing adsorption of the natural gas stream to selectively remove nitrogen and produce a highly concentrated methane product stream. Secondly, the waste gas from the first PSA unit is passed through a PSA process which contains an adsorbent selective for methane so as to produce a highly concentrated nitrogen product. One important feature of the patented invention is the nitrogen selective adsorbent in the first PSA unit. This adsorbent is a crystalline titanium silicate molecular sieve also developed by the present assignee. The adsorbent is based on ETS-4 which is described in commonly assigned U.S. Pat. No. 4,938,939. ETS-4 is a novel molecular sieve formed of octrahedrally coordinated titania chains which are linked by tetrahedral silicon oxide units. The ETS-4 and related materials are, accordingly, quite different from the prior art aluminosilicate zeolites which are formed from tetrahedrally coordinated aluminum oxide and silicon oxide units. A nitrogen selective adsorbent useful in the process described in U.S. Pat. No. 6,197,092 is an ETS-4 which has been exchanged with heavier alkaline earth cations, in particular, barium. It has also been found by the present assignee that in appropriate cation forms, the pores of ETS-4 can be made to systematically shrink from slightly larger than 4 Å to less than 3 Å during calcinations, while maintaining substantial sample crystallinity. These pores may be frozen at any intermediate size by ceasing thermal treatment at the appropriate point and returning to ambient temperatures. These materials having controlled pore sizes are referred to as CTS-1 (contracted titano silicate-1) and are described in commonly assigned U.S. Pat. No. 6,068,682, issued May 30, 2000, incorporated herein by reference in its entirety. The CTS-1 molecular sieve is particularly effective in separating nitrogen and acid gases selectively from methane as the pores of the CTS-1 molecular sieve can be shrunk to a size to effectively adsorb the smaller nitrogen and carbon dioxide and exclude the larger methane molecule. The barium-exchanged ETS-4 for use in the separation of nitrogen from a mixture of the same with methane is described in commonly assigned U.S. Pat. No. 5,989,316, issued Nov. 23, 1999. Reference is also made to U.S. Pat. No. 6,315,817 issued Nov. 13, 2001, which also describes a pressure swing adsorption process for removal of nitrogen from a mixture of same with methane and the use of the Ba ETS-4 and CTS-1 molecular sieves. Due to the ability of the ETS-4 compositions, including the CTS-1 molecular sieves for separating gases based on molecular size, these molecular sieves have been referred to as Molecular Gate® sieves.

An apparent disadvantage of using Molecular Gate® titanium silicate sieves in processes for the removal of nitrogen from natural gas is that approximately one-half of the propane and all the butane and heavier hydrocarbon components are co-adsorbed with the nitrogen. Thus, it has been found that the $C_{3+}$ hydrocarbons, although too large to be adsorbed in the pores of the Molecular Gate® sieves, are adsorbed on the exterior surfaces of the sieves and binder used to hold the sieves together to form a particle. On regeneration of the sieves during the PSA process, the nitrogen and $C_{3+}$ components are combined as a low pressure tail gas. The $C_{3+}$ components represent a loss of desirable heating value and additional chemical value when present in the tail gas.

Commonly assigned, co-pending application, U.S. Ser. No. 09/945,870, filed Sep. 4, 2001 is directed to an improved PSA process for removing $CO_2$ from natural gas streams. In general, the process involves an initial PSA separation with a carbon dioxide-selective adsorbent, the formation of an intermediate pressure vent stream such as methane and recycling of the vent stream to feed. $CO_2$-selective adsorbents include activated carbon, alumina, silica, and zeolite molecular sieves. A preferred $CO_2$-selective adsorbent is a silica gel marketed under the name PCS™ by Engelhard Corporation, Iselin, New Jersey. Unfortunately, similar to loss of hydrocarbons found with nitrogen removal using CTS-1 adsorbents, on regeneration of the $CO_2$ adsorbent, it has been found that $CO_{2+}$ hydrocarbons are combined with the carbon dioxide in the tail gas. Again, the $C_{2+}$ components in the tail gas represent a loss of desirable heating value and additional chemical value.

The majority of the market supply of $C_2$ and $C_{3+}$ hydrocarbons are extracted from natural gas. For this reason these components are commonly termed natural gas liquids (NGLs). The removal of the $C_{3+}$ hydrocarbons from natural gas is accomplished in three alternative routes.

In the first and oldest method, heavy oil is contacted with natural gas such that the lean oil wash absorbs $C_{3+}$ components into the liquid. These components are then stripped from the oil and eventually recovered as a separate product. More recent designs use refrigerated oil but overall this technology is considered outdated. A second method of recovery of $C_{3+}$ hydrocarbons is through a refrigeration system where the natural gas feed is chilled to temperatures typically in the range of −30° F. and the $C_{3+}$ components are substantially condensed from the natural gas stream. A more efficient, though more expensive, method and means to recover ethane as well, is generally applied to large gas flows where a turbo-expander plant expands the natural gas to a lower pressure. This expansion causes a substantial drop in the temperature of the natural gas stream. Once more, $C_{3+}$ hydrocarbons are removed. As a general rule turbo-expander plants are favored where ethane recovery is desired or higher levels of $C_{3+}$ liquids recovery is justified. These plants are expensive, especially for recompression. All of the routes for liquid recovery are fairly expensive in capital and require considerable power for either refrigeration or recompression.

The relationship in value of natural gas to natural gas liquids is complex and the prices, while related, do fluctuate. Almost always, the components are more valuable as a liquid than as a gas and a typical increase in value is about 1.5× the value in the pipeline. The extraction of liquids is the main business of mid-stream processors.

The present assignee has developed processes for the removal of nitrogen and recovery of hydrocarbons from natural gas utilizing pressure swing adsorption with Molecular Gate® sieves. These processes are described in co-pending applications, U.S. Ser. Nos. 09/699,664, filed Oct. 30, 2000, now U.S. Pat. No. 6,444,012, issued Sep. 3, 2002, and Ser. No. 09/793,039, filed Feb. 26, 2001, now U.S. Pat. No. 6,497,750, issued Dec. 24, 2002. In the former application, the PSA process involves initially adsorbing $C_{3+}$ hydrocarbons from a natural.gas stream in a first PSA unit containing a hydrocarbon-selective adsorbent to produce a first product stream comprising methane, nitrogen and reduced level of hydrocarbons relative to the feed. The first product stream is then directed to a second PSA adsorption unit containing a nitrogen selective adsorbent (Molecular Gate®) so as to adsorb nitrogen and produce a second product stream enriched with methane. Recovery of the hydrocarbons can be achieved by desorbing the first adsorbent with the methane product stream. In this way, the heat value of the $C_{3+}$ hydrocarbons is recaptured in the methane stream. The latter application is directed to a process of separating nitrogen from a feed natural gas stream in a first PSA unit containing a Molecular Gate® nitrogen-selective adsorbent to form a methane product stream, directing the tail gas from the first PSA unit to a second PSA unit containing a methane selective adsorbent so as to recover methane from the tail gas to form a nitrogen rich product stream and a tail gas stream comprising hydrocarbons and refrigerating the hydrocarbon-containing tail gas so as to knock out the $C_{3+}$ hydrocarbon liquids. The methane is then recycled to feed.

The process of the present invention which is described below, provides for both the effective removal of nitrogen and/or carbon dioxide from natural gas such as with a Molecular Gate® sieve and recovery of the $C_{3+}$ hydrocarbons which are also contained in the natural gas stream. The process of the present invention provides an alternative to previous processes for natural gas liquid recovery from natural gas streams as well as an alternative from the present assignee's own combined processes of nitrogen removal and hydrocarbon recovery from natural gas streams using pressure swing adsorption with Molecular Gate® sieves.

SUMMARY OF THE INVENTION

This invention provides a novel PSA system to remove nitrogen and/or carbon dioxide from natural gas. The PSA process of this invention to remove nitrogen/$CO_2$ from natural gas also achieves high system NGL recovery. In accordance with this invention, a natural gas feed is first passed through a nitrogen-selective adsorbent or $CO_2$-selective adsorbent, such as a Molecular Gate® titanium silicate adsorbent of the present assignee, to selectively remove nitrogen and/or $CO_2$ from the natural gas stream and produce a product rich in methane gas. Along with the adsorbed nitrogen and/or carbon dioxide, a significant portion of the $C_{3+}$ hydrocarbons are adsorbed on the exterior surface of the adsorbent. The $C_{3+}$ hydrocarbon recovery is achieved by directing the tail gas from the first PSA unit and which is concentrated in desorbed nitrogen and/or $CO_2$ and $C_{3+}$ hydrocarbons to a second Partial Pressure Swing /Pressure Swing adsorber unit which is selective for the hydrocarbons such as a carbon adsorbent. Note we refer to this unit as a partial pressure swing adsorber because the stream entering the bed on the purge step is not generated by the unit but is an external stream. The natural gas liquids are recovered from the adsorbent of the second PSA unit by desorption with a co-current intermediate pressure vent stream from the first PSA unit.

Subsequent to the adsorption of the nitrogen and/or $CO_2$ in the first PSA unit, one or more pressure equalization steps (depressurizing co-current to the feed) are conducted in which the methane is removed from the adsorber vessel in the step following adsorption and transferred into one or more other vessels undergoing purge or repressurization steps. Such pressure equalization and purge steps in a PSA process are well understood by those of ordinary skill in the art. In traditional PSA processing, at the end of such co-current depressurization steps, the adsorber vessel is depressurized in a direction counter-current to the feed stream and the impurity, in the case of the present invention, nitrogen and/or carbon dioxide, is partially removed. The removal of the impurity is further conducted by purging the bed, typically with a light gas component. In the present invention, rather than following the traditional co-current depressurization steps of equalization or provide purge with a counter-current blow down step, a step or steps of co-current depressurization is used in which the co-current depressurization stream substantially containing the desirable methane is removed at intermediate pressure and directed to the adsorbent in the second PSA unit which contains adsorbed $C_{3+}$ hydrocarbons. This co-current vent stream at intermediate pressure is able to desorb the NGL components from the adsorbent. The methane and other heavier hydrocarbons can then be separated by flash separation or refrigeration.

The co-current vent stream to the second PSA unit in the process of this invention allows the PSA system to recover natural gas liquids that would otherwise be lost in the tail gas stream of the first impurity-selective PSA unit and further allows the PSA system to further treat methane gas that would otherwise be lost during the blow down step. Accordingly, not only is NGL recovery provided, but overall methane recovery is increased. At the end of the co-current depressurization step, the traditional blow down followed by purge steps and subsequent re-pressurization can be conducted. It may also be desirable to conduct additional co-current depressurization steps such as equalizations after the co-current depressurization vent step.

DETAILED DESCRIPTION OF THE INVENTION

In general, the first stage of the process involves the adsorptive removal of nitrogen and carbon dioxide from the natural gas stream. Thus, the feed stream is passed through an adsorbent, such as the titanium silicate Molecular Gate® adsorbents of the present assignee to selectively adsorb nitrogen and $CO_2$ and produce a methane rich product stream. What has been found is that the titanium silicate adsorbents also adsorb the $C_{3+}$ hydrocarbons on the exterior surface of the adsorbent. Coadsorption of $C_{3+}$ hydrocarbons has also been found using silica gel adsorbents for removal of $CO_2$ from natural gas using PSA processes as disclosed in aforementioned U.S. Ser. No. 09/945,870. In the past, these hydrocarbons along with the nitrogen and $CO_2$ were desorbed from the adsorbent and passed through the low pressure waste stream wherein the heat and chemical values of the NGL components would be lost.

In the second stage of the process of this invention, the waste stream from the $N_2$/$CO_2$-selective adsorbent, containing desorbed nitrogen, carbon dioxide and $C_{3+}$ hydrocarbons is passed through a hydrocarbon-selective adsorbent, which adsorbs primarily heavier hydrocarbons. An important feature of the present invention is the recovery of the $C_{3+}$ hydrocarbons from the hydrocarbon-selective adsorbent bed by purging the second stage bed with a co-current, intermediate pressure vent stream from the first PSA unit. This vent stream which contains methane and desorbs the heavier hydrocarbons from the hydrocarbon-selective adsorbent at a pressure higher than waste gas pressure. The desorbed hydrocarbons can then be pressurized and treated so as to separate the natural gas liquids from methane. Recycle steps in many PSA systems are often referred to as rinse steps and consist of recycling waste back to the feed. However, compression requirements for recycling waste gas to feed pressure are significantly higher than for the vent stream of this invention as a typical waste stream is available at pressure under 10 psia while the co-current vent stream is available at a higher pressure of at least 15 psia. Those skilled in the art will recognize that compression requirements scale with the inverse of the suction pressure. Subsequent to NGL separation, any methane can be recycled to feed, thus improving the overall methane recovery of the process while at the same time, recovering the $C_{3+}$.

Figure 1:
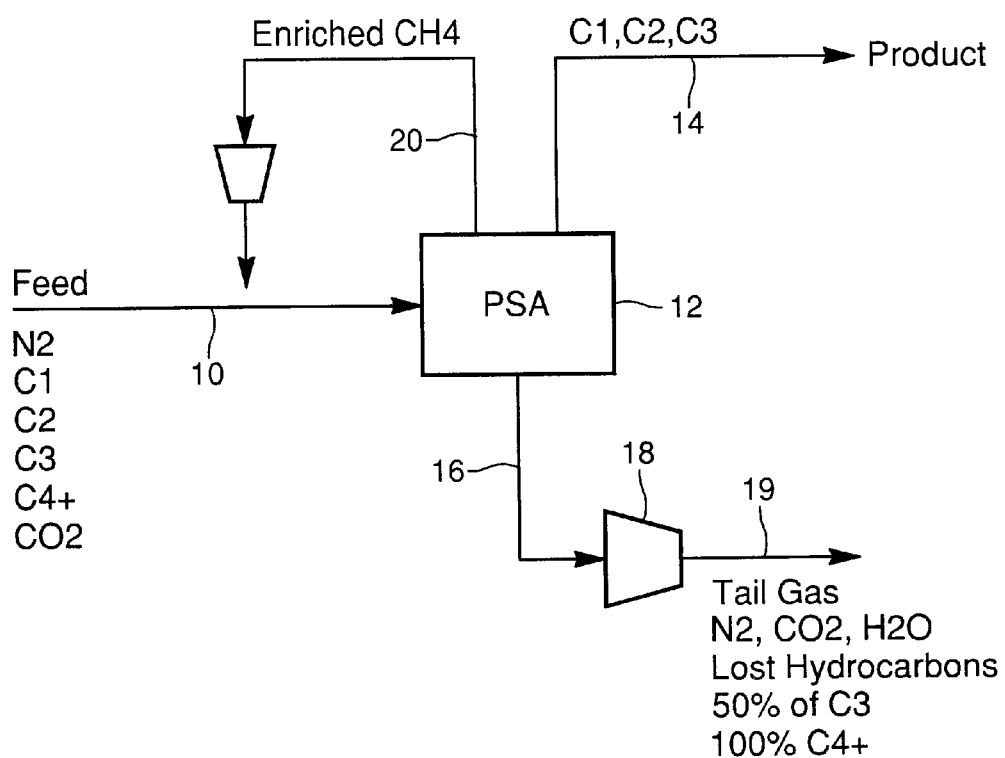
FIG. 1 is a schematic of a prior art PSA process for selectively removing nitrogen and carbon dioxide from methane and wherein the tail gas contains significant levels of NGL components.

FIG. 1 illustrates a typical PSA process for the removal of impurities from methane. In such process, a feed stream 10 containing methane, nitrogen, carbon dioxide and hydrocarbons such as ethane, propane, butane, and heavier hydrocarbons at a feed pressure of about 100 to 800 psia is directed to a PSA unit 12 which contains a nitrogen and/or $CO_2$ selective adsorbent. Particularly useful nitrogen-selective adsorbents are the titanium silicate Molecular Gate® molecular sieves such as modified ETS-4 and related materials discovered by the present assignee. PSA unit 12 produces a product stream 14 which is a highly purified methane stream and which is not adsorbed on the adsorbent in PSA unit 12. Typically, the concentration of methane in stream 14 is greater than 90 mol %, preferably greater than 95 mol % methane. Desorption of nitrogen and carbon dioxide which were initially adsorbed by the adsorbent in PSA 12 creates a low pressure waste gas stream 16, typically at a pressure less than 10 psia, containing nitrogen, polar gas such as carbon dioxide and water if present in the feed and typically about 50% of the $C_3$ hydrocarbons and about 100% of the $C_4$ and heavier hydrocarbons which were present in feed stream 10. The waste stream 16 is typically pressurized in compressor 18 to pressures of 15 to 45 psia as a tail gas 19. The $C_{3+}$ hydrocarbon content of this tail gas represents lost heating value as well as lost chemical value from these heavy hydrocarbon sources. As previously stated, adsorbents other than titanium silicates, such as silica gels or activated carbons for selectively adsorbing $CO_2$, also coadsorb hydrocarbon values from natural gas streams.

Also shown in FIG. 1 is an important feature for improving the overall methane recovery and PSA process efficiency and which is disclosed in aforementioned U.S. Ser. No. 09/699,664, now aforementioned U.S. Pat. No. 6,444,012. This feature is the vent recycle stream 20 which is a co-current intermediate pressure stream which is taken to recycle methane contained within the void spaces of the adsorbent bed in PSA stage 12. By taking the intermediate pressure stream, at about 30 psia, compression costs to compress to feed pressure are greatly reduced relative to taking a waste stream, typically at less than 10 psia and recycling a portion at feed pressure. While an important step in improving PSA process efficiency in recovering a purified methane product stream, the intermediate pressure vent stream does not otherwise solve the problem of recovering the heavy hydrocarbons which are adsorbed on the exterior surface of the adsorbent.

Figure 2:
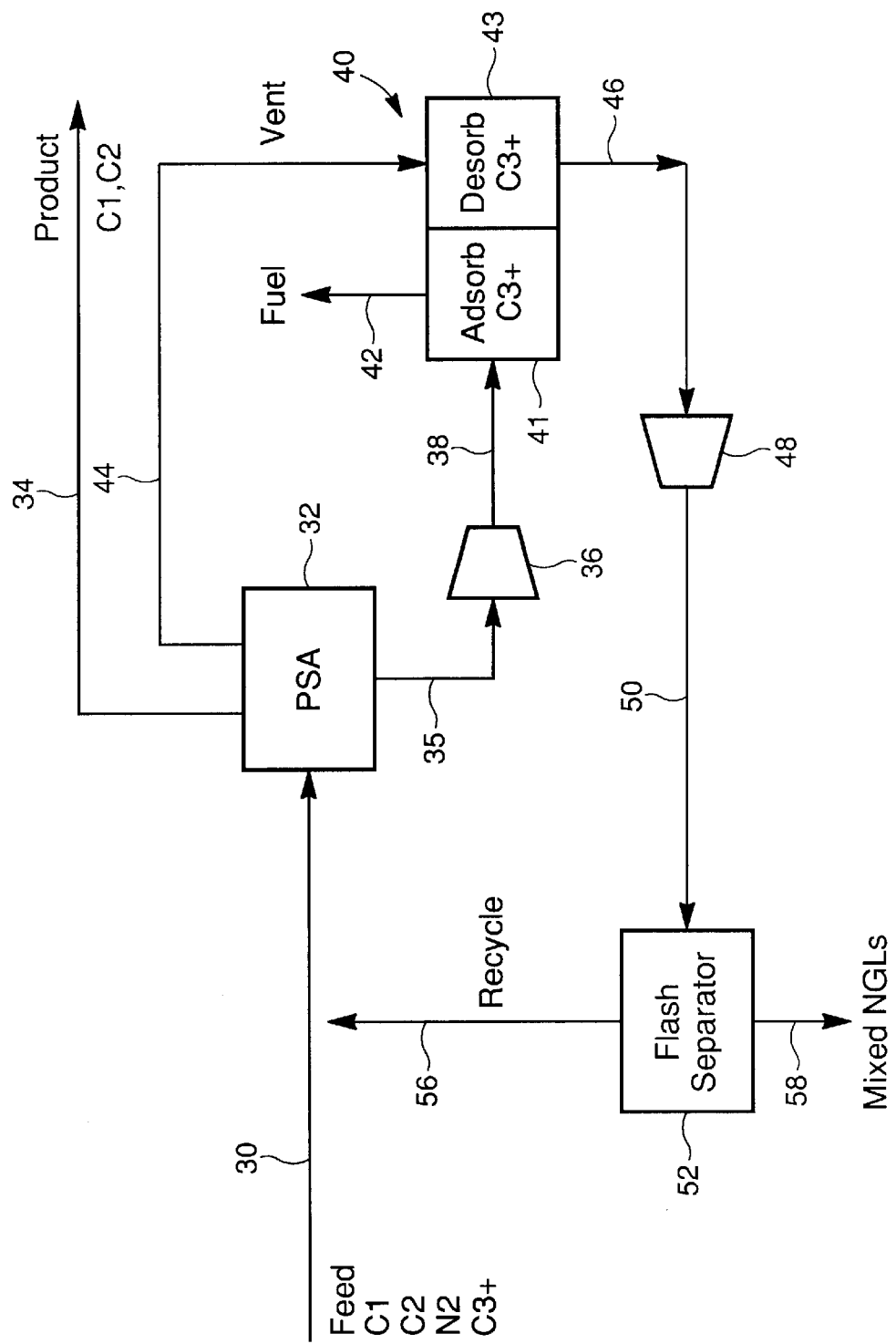
FIGS. 2 and 3 represent schematics of the process of the present invention which illustrate the removal of nitrogen and carbon dioxide from natural gas and the recovery of NGL components.
Figure 3:
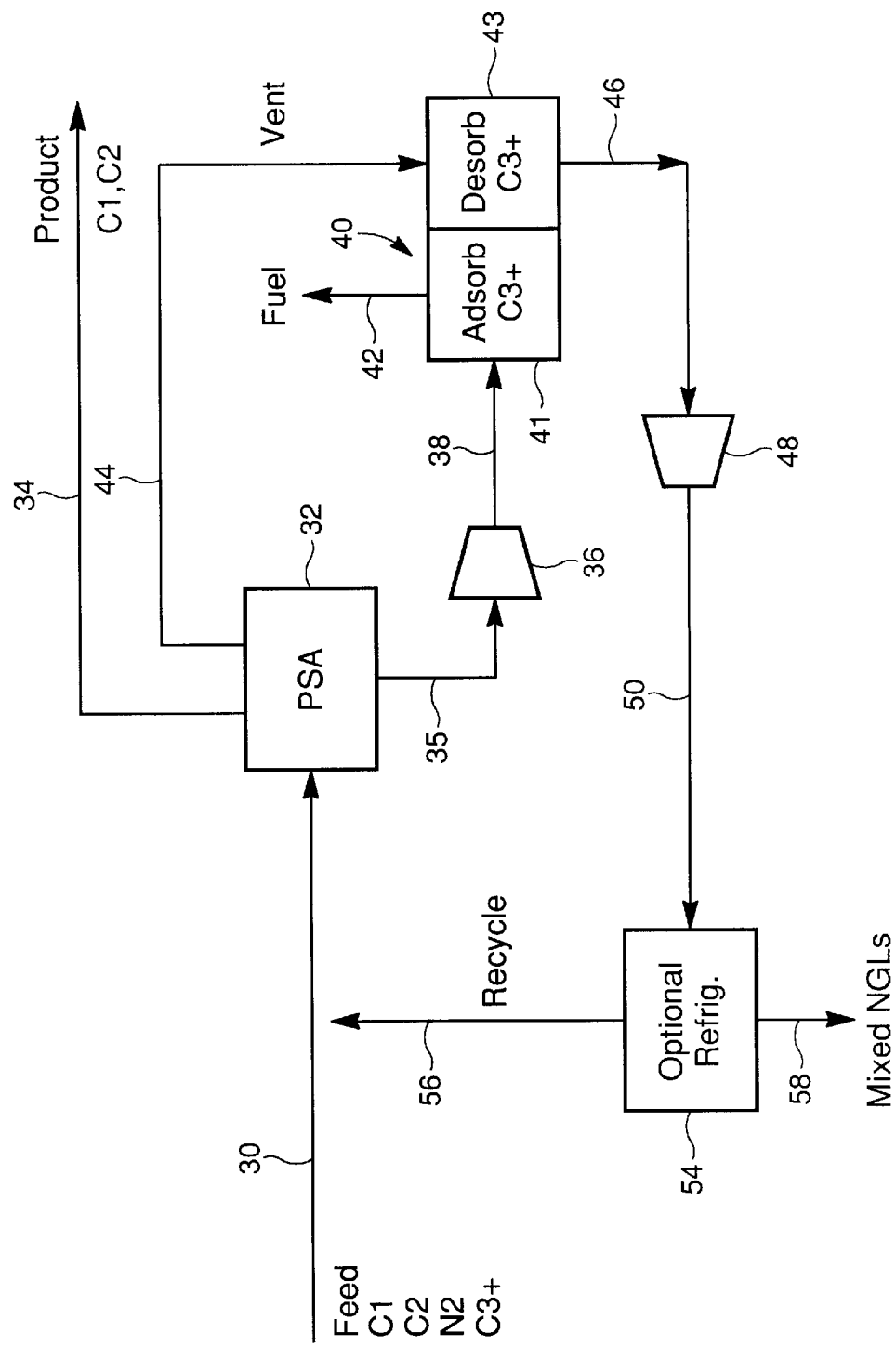

The process of the present invention directed to separating nitrogen and/or carbon dioxide from natural gas streams by pressure swing adsorption and the recovery of natural gas liquids from the feed stream can be described by referring to FIGS. 2 and 3. These two figures are essentially identical except for the final separation of the natural gas liquids from methane. Referring to FIGS. 2 and 3, feed stream 30, identical to feed stream 10 shown in FIG. 1 is directed to pressure swing adsorption unit 32 which contains one or more adsorbents selective for nitrogen and/or carbon dioxide such as those described previously. Particularly preferred adsorbents are the titanium silicate molecular sieves known as Molecular Gate® sieves developed by the present assignee. A particularly preferred adsorbent for $CO_2$ only includes a silica gel such as PCS™. As disclosed in commonly assigned U.S. Pat. No. 6,086,682, it has been discovered that cationic forms of ETS-4 can be transformed into CTS-1 by heating. Preferably, ETS-4 in the strontium or calcium form with or without low levels of sodium is heated at temperatures ranging from about 50° C. to 450° C., preferably 200° C. to 350° C. for 0.5 to 100 or more hours, preferably 24–48 hours, then cooled in order to lock in the desired pore size. Cooling can be accomplished in an air stream, which is free of $CO_2$ and water. Other inert gases may be used as long as such gases are free of $CO_2$ and water. The calcination temperature used to achieve a desired pore diameter depends on the cations present in the reagent ETS-4. Although multivalent strontium and calcium are the preferred cations for CTS-1, other cations can be used with appropriate changes of temperatures and durations of thermal treatment. Various combinations of Sr, Ca, Li, Mg, Na, H, Ba, Y, La, and/or Zn have all demonstrated separation selectivities. Additionally the CTS-1 materials can be back-exchanged with metal, ammonium, or hydrogen ions in a conventional manner if such is desired.

Also useful as a Molecular Gate adsorbent is barium-exchanged ETS-4 without pore contraction via calcination. This material is explicitly disclosed in aforementioned U.S. Pat. No. 5,989,316. The barium-exchanged ETS-4 is prepared by contacting ETS-4 with an inorganic salt of barium in order to affect the desired exchange. Still further, the ETS-4 exchanged with a mixture of multivalent cations, with or without barium is also useful. Non-limiting examples of such multivalent cations include Sr, Ca, Mg, and Zn.

The ETS-4 which is used as the starting material can be prepared in accordance with the teachings of U.S. Pat. No. 4,938,939 wherein the haloid-containing reactants are used or can be prepared from reaction mixtures which are free from haloid-containing reactants in a manner analogous to the preparations of ETS-10 as set forth in U.S. Pat. No. 5,453,263, the entire disclosures of which are incorporated herein by reference.

It is also within the scope of this invention to use a mixture of the above adsorbents in the first PSA unit to adsorb both nitrogen and $CO_2$ and allow the controlling of costs with respect to the adsorbent. In still a further aspect of this invention, it may be useful to include in the first PSA unit an adsorbent which is selective for $C_{3+}$ hydrocarbons relative to methane so as to enhance the recovery of NGLs from the natural gas feed stream. Desorption into the waste of the first PSA unit stream and eventual selective re-adsorption in the second adsorption unit, allows improved capture of NGLs from the feed stream into the methane vent stream. Final separation from methane provides full recovery of NGLs from the feed stream. Since typical carbon dioxide adsorbents will also selectively adsorb hydrocarbons the mixture containing a hydrocarbon-selective adsorbent will most likely be used with a nitrogen-selective adsorbent including the CTS-1 materials described above. Thus, mixed with the nitrogen-selective adsorbent can be an adsorbent which is selective for $C_{3+}$ hydrocarbons relative to methane. Non-limiting examples of such adsorbents include activated carbon, silica gels, ZnX and alumina adsorbents, which have a selectivity of $C_{3+}$ over methane. While typical carbon dioxide-selective adsorbents are also effective to adsorb hydrocarbons, still mixtures of activated carbon, silica gel, ZnX and alumina can be used to adsorb carbon dioxide and to provide enhanced adsorption of $C_{3+}$ hydrocarbons from the natural gas feed stream. Such mixtures allow process variability to balance adsorbent and/or operational costs.

Referring again to FIGS. 2 and 3, the adsorbent effectively removes the nitrogen and carbon dioxide from the natural gas stream to yield a product stream 34 which typically contains over 90 mol. % methane. Minor amounts of $C_2$ and $C_3$ hydrocarbons may be contained in product stream 34. As described previously, it has been found that typically about 50% of the $C_3$ hydrocarbons and substantially all of the $C_{4+}$ are adsorbed on the titanium silicate molecular sieves. The adsorption of the heavier hydrocarbon is not due to size selectivity as is the case in the adsorption of nitrogen and $CO_2$ which are adsorbed in the pores of the sieve since the pores of the sieves such as in CTS-1 are sized to accept nitrogen and $CO_2$ and not the larger methane or other hydrocarbon molecules. The $C_{3+}$ hydrocarbons instead are adsorbed on the exterior surface of the titanium silicate molecular sieve believed due to electronic attractive forces between the heavy hydrocarbons and the sieve. Thus, upon conventional de-pressurization/desorption of PSA unit 32, a waste gas stream 35 containing desorbed nitrogen, and carbon dioxide and most of the $C_{3+}$ hydrocarbon content of the feed stream is formed.

If only $CO_2$ is present in the natural gas stream, i.e. the nitrogen content is less than 4 mol %, or if one wishes to remove only $CO_2$ from the natural gas stream, an alternative to the titanium silicate molecular gate® adsorbent that can be used is PCS™, a silica gel adsorbent. This particular adsorbent, contains a higher micropore volume than similar silica gel adsorbents. Thus, the micropore volume ($cm^3/g$) as % intrusion volume is at least 15%, measured by the AutoPore IV 9500, (Hg Porosimetry) and TriStar 3000 (N2 Porosimetry), both from Micrometrics, Norcross, Ga. This percent of micropore volume relative to the total pore volume is believed higher than known commercial silica gel adsorbents. The PCS™ adsorbent also has a higher uptake of carbon dioxide as shown in $CO_2$ isotherms compared with other silica gel adsorbents. It is believed,that the micropore volume provides the improved $CO_2$ uptake of this particular silica adsorbent. Table 1 sets forth the properties of PCS™. Table 2 is a comparison of silica adsorbent PCS™ with a commercial silica adsorbent, Sorbead R, from Engelhard Corporation. Further many other adsorbents demonstrate an equilibrium selectivity for $CO_2$ over $CH_4$. Some such adsorbents include activated carbon, carbon molecular sieve, and Clinoptilites.

TABLE 1

|  |  | PCS ™ |
| --- | --- | --- |
| Regeneration Temp | ° C. | 170 |
| BET surface area | m2/g | 756 |
| Micropores | % | 15 |
| Pore Volume | cm3/g | 0.48 |
| Average Pore Diameter | nm | 2.5 |
| Water Adsorption at 25° C. and |  |  |
| 10% r.H. % |  | 7.2 |
| 80% r.H. % |  | 42.9 |
| XFA | % | >99 |
| SiO2 |  |  |
| Al2O3 | % | <0.5 |
| Na | % | <0.05 |
| Packed Density | kg/l | 0.64 |

TABLE 2

|  | Sorbead R | PCS ™ |
| --- | --- | --- |
| Pore Volume (1000–20000A) as % Intrusion Volume[1] | 2.47% | 25.27% |
| Micropore Volume as % of Intrusion Volume[2] | 4.90% | 22.96% |

[1]Hg Porosimetry AutoPore IV 9500, Micromeritics, Norcross, GA
[2]N2 Porosimetry TriStar 3000, Micromeritics, Norcross, GA If PCS™ is used, then $C_{3+}$ hydrocarbons are preferentially adsorbed over $C_1$ hydrocarbons throughout the adsorbent at levels approximately equal to or greater than carbon dioxide. Low pressure waste stream 35 is pressurized via compressor 36 to a feed stream 38 which is directed to a second PSA unit 40. PSA unit 40 contains a hydrocarbon-selective adsorbent such as carbon which adsorbs the hydrocarbons in the waste gas which had been purged from the void space of the adsorbent bed in PSA unit 32 and the natural gas liquids which were desorbed from the surface of the adsorbent bed in PSA unit 32. Other hydrocarbon adsorbents include crystalline aluminosilicate zeolites such as 13X or a high aluminum X or an amorphous adsorbent such as silica gel. A particular preferred silica gel is Sorbead® available from Engelhard Corporation. A fuel stream 42 comprising a high concentration of nitrogen and or $CO_2$ which is not adsorbed in PPSA/PSA unit 40 can be recovered. If stream 42 contains non-adsorbed hydrocarbons, stream 42 can be used as a fuel stream.

Recovery of the natural gas liquids from the adsorbent bed in PSA/PPSA unit 40 is achieved by forming a co-current, intermediate pressure vent stream 44 from PSA unit 32 which contains a high concentration of methane captured from the void space of the adsorbent bed in PPSA/PSA unit 32. The vent stream at a pressure intermediate of the pressure of product stream 34 and waste stream 35 is contacted with the hydrocarbon-selective adsorbent in PPSA/PSA unit 40 so as to desorb the hydrocarbons from the adsorbent to form stream 46. Stream 46 is pressurized via compressor 48 to form mixed NGL stream 50 which also contains methane. The natural gas liquids can be separated from the lighter methane by any known method in the art. In FIG. 2 is shown flash separator 52 whereas in FIG. 3 is shown refrigeration unit 54 to provide separation of methane from the NGLs. The natural gas liquids 58 can be condensed or otherwise separated from the methane component in any known manner. The methane can be recycled to feed stream 30 via recycle line 56.

Regarding the specific operation of PSA 32, the following steps are followed: adsorption, equalization, co-current depressurization to compression, provide purge, fuel, countercurrent depressurization, purge, equalization and pressurization. These steps are well-known to those of ordinary skill in this art. Reference is again made to U.S. Pat. Nos. 3,430,418; 3,738,087 and 4,589,888 for a discussion of these internal steps of a PSA process. The adsorption process in PSA unit 32, begins with the nitrogen adsorption step in which gas stream 30 at a pressure of about 100–800 psia, a temperature of 70–900° F., and typically containing 4–30 mol. % nitrogen, 2–15 mol % carbon dioxide, and 5–20 mol. % $C_{2+}$ hydrocarbons (4–15 mol. % $C_{3+}$), is fed to a bed containing a nitrogen and/or $CO_2$-selective adsorbent. At nitrogen levels less than 4.0 mol. % and $CO_2$ levels of less than 2.0 mol. %, generally pipeline specifications are met and there is no need to separate these impurities, unless total impurity ($N_2+CO_2$) levels are greater than 4.0 mol. %.

Nitrogen and/or $CO_2$ adsorption yields a product stream 34 rich in methane, reduced in nitrogen and $CO_2$ and at approximately the same operational pressure as feed 30. After the adsorption step, the bed is co-currently depressurized in a series of steps referred to in the art as equalizations or to provide purge gas to a vessel undergoing regeneration. After the adsorbent bed has completed 1 to 4 equalizations, the adsorbent bed can be further co-currently depressurized. The gas leaving the bed during the co-current depressurization, depicted as stream 44 can be used as either fuel, provide purge, recycled back to feed or any combination thereof. In this invention, co-current vent stream 44 is used to desorb $C_{3+}$ hydrocarbons from the adsorbent in PSA unit 40 and forms stream 46 containing NGLs and methane. Stream 44 will have a pressure of 20 to 100 psia, preferably 30 to 60 psia. Subsequently, the bed in PSA unit 32 is counter-currently depressurized, and then purged with gas from the earlier provide purge step. The adsorbent bed is pressurized with gas from earlier equalizations, and finally the bed is pressurized with product gas or alternatively feed gas. These steps are routine, and except for directing the co-current intermediate pressure vent stream 44 to desorb PPSA/PSA Unit 40 are known in the art. This latter step is unique and important for $C_{3+}$ recovery and overall process efficiency including improvement in operational costs. By using a co-current vent stream for desorption instead of a portion of the waste stream, operational energy costs (compression costs) are saved as the vent stream 44 is compressed to sufficient pressure for NGL separation from a higher pressure than would be a waste stream portion. Subsequent to desorption with vent stream 44, a further depressurization/equalization step to about 20 psia can be performed to recover methane from void space gas before a final purge to waste gas 35 at low pressure, e.g. 7 psia.

It has been found that the performance of the nitrogen-selective titanium silicate molecular sieves in PSA unit 32 varies over time. After an initial 1 hour start-up period, PSA unit 32 starts producing a higher purity methane product stream than the average purity. Subsequently, methane purity in the product stream 34 steadily drops. After 12 hours the purity of the product stream can drop below acceptable purity.

Periodically heating the adsorbent bed in PSA unit 32 increases the nitrogen working capacity (amount of nitrogen adsorbed/desorbed each cycle) of PSA 32. It is believed that this is accomplished by lowering the methane loading on the adsorbent. The loss in nitrogen working capacity is illustrated by the lowering of product purity at a fixed product draw rate. This performance decline vs. time can be mitigated by periodically heating/cooling a bed(s) in PSA 32. PSA 32 can be cooled for 1.5 hours to 70° F. with nitrogen or product methane. After the cooling period is completed, the adsorbent bed in PSA 32 can again be fed the feed gas. It has been shown that subsequent to the heating and cooling cycle, the purity of the methane product jumps to the desired methane purity.

More specific process parameters are now given with respect to the operation of PSA unit 40 which adsorbs hydrocarbon values from waste stream 35. Again, referring to FIGS. 2 and 3, PSA 40 is used to recover $C_{3+}$ hydrocarbons which are co-adsorbed on the nitrogen/$CO_2$-selective adsorbent in PSA unit 32 and recovered within the methane-rich, co-current vent stream 44. Operation of PSA 40 is as follows. In the first step, column 41 containing a hydrocarbon selective adsorbent is fed stream 38 which has been compressed from waste stream 35 at a pressure less than 10 psia to an elevated pressure up to about 40 psia. The product gas, stream 42, leaving the adsorbent bed 41 in this step is a concentrated nitrogen and/or carbon dioxide stream typically at or slightly below feed pressure. Upon completion of the $C_{3+}$ hydrocarbon adsorption step, the bed (as depicted in column 43) is purged with the methane-rich vent gas 44 produced from the vent step in PSA 32. During the purging step, the $C_{3+}$ hydrocarbons which have been adsorbed during the hydrocarbon adsorption step are removed or desorbed from the adsorbent and leave PSA stage 43 mixed with the methane rich product gas via stream 46 at a pressure slightly below the pressure of vent stream 44.

Stream 46 containing about 20 to 65 mol. % methane and 5 to 40 mol. % $C_{3+}$ hydrocarbons are compressed to approximately feed pressure in compressor 48 and directed to separation whereby the compressed stream is cooled so as to condense heavier hydrocarbons from the lighter gas phase. This gas phase, including methane and $C_2$ values can be recycled to feed 30 via line 56.

EXAMPLE 1

Using pilot plant data, i.e. balances around the first PSA unit containing CTS-1 and the hydrocarbon adsorption unit containing activated carbon, a calculation of NGLs present in each stream was made. See Table 3 for operational variables and compositions of each stream as depicted in FIGS. 2 or 3.

TABLE 3

|  | Raw Feed | MG Product | Tail Gas | Vent | Liquids | Waste |
|---|---|---|---|---|---|---|
| Flow, MM SCFD | 10.00 | 8.28 | 0.97 | 0.98 | 0.21 | 0.75 |
| Flow, lbmol/hr | 1189 | 984 | 115 | 116 | 25 | 89 |
| Pressure, psia | 400 | 385 | 40 | 400 | 400 | 35 |
| Temp., F. | 85 | 85 | 85 | 85 | 85 | 85 |
| C1 | 85.71 | 92.21 | 43.80 | 87.92 | 9.28 | 62.77 |
| C2 | 5.31 | 3.85 | 9.87 | 4.62 | 8.45 | 12.05 |
| C3 | 2.60 | 0.94 | 8.45 | 1.65 | 24.08 | 3.16 |
| C4 | 1.38 | 0 | 14.20 | 0.84 | 36.74 | 0 |
| C5 | 0.22 | 0 | 2.25 | 0.18 | 7.93 | 0 |
| C6+ | 0.31 | 0 | 3.20 | 0.30 | 13.09 | 0 |
| N2 | 4.23 | 3.00 | 15.73 | 4.28 | 0.22 | 19.55 |
| CO2 | 0.24 | 0 | 2.49 | 0.20 | 0.21 | 2.46 |

Once given the above disclosure, many other features, modifications, and improvements will become apparent to the skilled artisan. Such other features, modifications, and improvements are, therefore, considered to be a part of this invention, the scope of which is to be determined by the following claims.

We claim:

1. A process for the separation of nitrogen, carbon dioxide or both from a natural gas feed stream, and the recovery of hydrocarbons from said feed stream which comprises:

passing said natural gas feed stream to a first pressure swing adsorption unit containing an adsorbent selective for nitrogen, carbon dioxide or both so as to preferentially adsorb nitrogen, carbon dioxide or both from said feed stream and produce a first product stream enriched with methane and a low pressure waste stream having a higher molar concentration of nitrogen, carbon dioxide or both than said feed stream, said waste stream further containing a portion of said hydrocarbons contained in said feed stream and which have been co-adsorbed on said adsorbent;

passing said waste stream to a second adsorption unit containing a hydrocarbon-selective adsorbent so as to preferentially adsorb said co-adsorbed hydrocarbons to produce a second product stream enriched with nitrogen, carbon dioxide or both; and directing a methane-containing stream to said second adsorption unit to purge said hydrocarbon-selective adsorbent and produce a combined stream of methane and said co-adsorbed hydrocarbons adsorbed by said hydrocarbon-selective adsorbent.

2. The process of claim 1, wherein said hydrocarbons contained in said natural gas feed stream comprise $C_3+$hydrocarbons and said hydrocarbons co-adsorbed on said adsorbent comprise $C_4+$hydrocarbons.

3. The process of claim 2, wherein said hydrocarbons co-adsorbed on said adsorbent further include $C_3$ hydrocarbons.

4. The process of claim 1, wherein said methane-containing stream used to purge said hydrocarbon-selective adsorbent is obtained from said first pressure swing adsorption unit subsequent to formation of said first product stream, said methane-containing stream having a pressure lower than said first product stream.

5. The process of claim 4, wherein said methane-containing stream for purging said hydrocarbon-selective adsorbent is provided by co-currently depressurizing said first pressure swing adsorption unit to form a methane-containing stream having a pressure lower than said first product stream and a pressure higher than said waste stream.

6. The process of claim 5, wherein said product stream is at a pressure of 100 to 800 psia, said waste stream is at a pressure of less than 10 psia and said methane-containing stream is at a pressure of 20 to 100 psia.

7. The process of claim 5, wherein said adsorbent in said first pressure swing absorption unit is a crystalline titanium silicate molecular sieve.

8. The process of claim 7, wherein said molecular sieve is CTS-1.

9. The process of claim 7, wherein said molecular sieve is barium-ETS-4.

10. The process of claim 5 wherein said adsorbent in said first pressure swing adsorption unit is selective for carbon dioxide.

11. The process of claim 10 wherein said natural gas feed stream contains less than 4 mol. % nitrogen.

12. The process of claim 1, wherein said adsorbent in said first pressure swing adsorption unit is a crystalline titanium silicate molecular sieve.

13. The process of claim 12, wherein said molecular sieve is CTS-1.

14. The process of claim 12, wherein said molecular sieve is barium-ETS-4.

15. The process of claim 1, wherein said hydrocarbon-selective absorbent is an amorphous carbon or silica gel adsorbent.

16. The process of claim 1 wherein said adsorbent in said first pressure swing adsorption unit is selective for carbon dioxide.

17. The process of claim 16 wherein said adsorbent selective for carbon dioxide is a silica gel.

18. The process of claim 16 wherein said adsorbent selective for carbon dioxide is activated carbon.

19. The process of claim 16 wherein said natural gas feed stream contains less than 4 mol. % nitrogen.

20. The process of claim 19 wherein said adsorbent selective for carbon dioxide is a silica gel.

21. The process of claim 1 wherein said first adsorbent in said first pressure swing adsorbent unit contains a mixture of CTS-1 and an equilibrium adsorbent wherein said equilibrium adsorbent has a greater affinity for $C_{3+}$ hydrocarbon over methane.

22. The process of claim 21 where said equilibrium adsorbent is silica gel, ZnX, activated carbon or alumina.

23. The process of claim 1, wherein said first product stream contains over 90 mol. % methane.

24. The process of claim 1, comprising subsequent to forming said combined stream of methane and co-adsorbed hydrocarbons, separating said co-adsorbed hydrocarbons from said combined stream.

25. The process of claim 24, wherein said co-adsorbed hydrocarbons comprise $C_3+$hydrocarbons and separating said $C_3+$hydrocarbons from said combined stream by condensing said $C_3+$hydrocarbons.

26. The process of claim 1, wherein said natural gas feed stream contains 4 to 15 mol. % $C_3+$hydrocarbons.

27. The process of claim 1, wherein said natural gas feed stream contains greater than 4 mol. % nitrogen.

28. A process for the separation of nitrogen, carbon dioxide or both from a natural gas feed stream, and the recovery of $C_3+$hydrocarbons from said feed stream, which comprises:

passing said natural gas feed stream to a first pressure swing adsorption unit containing a crystalline titanium silicate, adsorbent so as to preferentially adsorb nitrogen and carbon dioxide and produce a first product stream containing at least 90 mol. % methane and a low pressure waste stream having a higher molar concentration of nitrogen and carbon dioxide than said feed stream, said waste stream further containing a portion of said $C_3+$hydrocarbons contained in said feed stream and which have been co-adsorbed on said titanium silicate adsorbent;

passing said waste stream to a second adsorption unit containing a hydrocarbon-selective adsorbent so as to preferentially adsorb said co-adsorbed $C_3+$hydrocarbons to produce a second product stream enriched with nitrogen and carbon dioxide; and directing a methane-containing stream having a pressure intermediate the pressure of said first product stream and said waste stream to said second adsorption unit to purge said hydrocarbon-selective adsorbent and produce a combined stream of methane and said co-adsorbed $C_3+$hydrocarbons adsorbed by said hydrocarbon-selective adsorbent.

29. The process of claim 28 wherein said crystalline titanium silicate is CTS-1 or an alkaline earth-exchanged ETS-4.

30. The process of claim 29 wherein said natural gas feed stream contains greater than 2 mol. % carbon dioxide, said first pressure swing adsorption unit further containing a silica gel carbon dioxide-selective adsorbent.

31. The process of claim 29 wherein said natural gas feed stream contains greater than 2 mol. % carbon dioxide, said first pressure swing adsorption unit further containing an activated carbon or carbon molecular sieve carbon dioxide-selective adsorbent.

32. The process of claim 28 wherein said natural gas feed stream contains greater than 4 mol. % nitrogen.

33. The process of claim 28 wherein said natural gas feed stream contains less than 2 mol. % carbon dioxide.

34. The process of claim 28 wherein said natural gas feed stream contains greater than 2 mol. % carbon dioxide, said first pressure swing adsorption unit further containing a silica gel carbon dioxide-selective adsorbent.

35. The process of claim 28 wherein said natural gas feed stream contains greater than 2 mol. % carbon dioxide, said first pressure swing adsorption unit further containing an activated carbon or carbon molecular sieve carbon dioxide-selective adsorbent.

36. The process of claim 28 wherein said first pressure swing adsorption unit contains an additional adsorbent which has a selectivity for $C_{3+}$ hydrocarbons greater than a selectivity for methane.

37. The process of claim 36 wherein said additional adsorbent is a silica gel, ZnX, activated carbon or alumina.

38. A process for the separation of carbon dioxide from a natural gas feed stream, and the recovery of $C_3$+hydrocarbons from said feed stream, which comprises:

passing said natural gas feed stream to a first pressure swing adsorption unit containing a silica gel adsorbent so as to preferentially adsorb carbon dioxide and produce a first product stream containing at least 90 mol. % methane and a low pressure waste stream having a higher molar concentration of carbon dioxide than said feed stream, said waste stream further containing a portion of said $C_3$+hydrocarbons contained in said feed stream and which have been co-adsorbed on said silica gel adsorbent;

passing said waste stream to a second adsorption unit containing a hydrocarbon-selective adsorbent so as to preferentially adsorb said co-adsorbed $C_3$+hydrocarbons to produce a second product stream enriched with carbon dioxide; and directing a methane-containing stream having a pressure intermediate the pressure of said first product stream and said waste stream to said swing adsorption unit to purge said hydrocarbon-selective adsorbent and produce a combined stream of methane and said co-adsorbed $C_3$+hydrocarbons adsorbed by said hydrocarbon-selective adsorbent.

39. The process of claim 38 wherein said natural gas feed stream contains less than 4 mol. % nitrogen and greater than 2 mol. % carbon dioxide.

40. The process of claim 39 wherein said natural gas feed stream contains at least 4 mol. % carbon dioxide.

41. The process of claim 38 wherein said first pressure swing adsorption unit contains an additional adsorbent which has a selectivity for $C_{3+}$ hydrocarbons greater than a selectivity for methane.

42. The process of claim 41 wherein said additional adsorbent is a silica gel, ZnX, activated carbon or alumina.

* * * * *

UNITED STATES PATENT AND TRADEMARK OFFICE
CERTIFICATE OF CORRECTION

PATENT NO.    : 6,610,124 B1
DATED         : August 26, 2003
INVENTOR(S)   : William Bachop Dolan and Michael J. Mitariten It is certified that error appears in the above-identified patent and that said Letters Patent is hereby corrected as shown below:

<u>Column 15,</u>
Lines 47-48, should read:

14. The process of claim 12, wherein said molecular sieve is barium-exchanged ETS-4.

Signed and Sealed this

Sixteenth Day of December, 2003

JAMES E. ROGAN
*Director of the United States Patent and Trademark Office*